US008236918B2

(12) United States Patent
Mueh et al.

(10) Patent No.: US 8,236,918 B2
(45) Date of Patent: Aug. 7, 2012

(54) POLYETHER-FUNCTIONAL SILOXANES, POLYETHER SILOXANE-CONTAINING COMPOSITIONS, METHODS FOR THE PRODUCTION THEREOF AND USE THEREOF

(75) Inventors: Ekkehard Mueh, Rheinfelden (DE); Peter Jenkner, Rheinfelden (DE); Max Preisenberger, Frankfurt am Main (DE); Burkhard Standke, Loerrach (DE)

(73) Assignee: Evonik Degussa GmbH, Essen (DE)

( * ) Notice: Subject to any disclaimer, the term of this patent is extended or adjusted under 35 U.S.C. 154(b) by 175 days.

(21) Appl. No.: 11/576,504

(22) PCT Filed: Nov. 5, 2004

(86) PCT No.: PCT/EP2004/052832
§ 371 (c)(1),
(2), (4) Date: Apr. 2, 2007

(87) PCT Pub. No.: WO2006/037380
PCT Pub. Date: Apr. 13, 2006

(65) Prior Publication Data
US 2009/0030162 A1 Jan. 29, 2009

(30) Foreign Application Priority Data
Oct. 8, 2004 (DE) .......................... 10 2004 049 427

(51) Int. Cl.
*C08G 77/26* (2006.01)
*C08G 77/00* (2006.01)
*C08G 77/04* (2006.01)
*C08G 77/14* (2006.01)
*C08G 77/22* (2006.01)

(52) U.S. Cl. ................ 528/38; 528/10; 528/30
(58) Field of Classification Search .......... 525/477
See application file for complete search history.

(56) References Cited

U.S. PATENT DOCUMENTS

| 3,567,753 | A | * | 3/1971 | Delaval et al. ............. 556/416 |
| 3,730,905 | A | * | 5/1973 | Koerner et al. ........ 427/213.34 |
| 3,793,360 | A | * | 2/1974 | Prokai et al. ............. 556/420 |
| 3,828,087 | A | * | 8/1974 | Pittman et al. ........... 556/439 |
| 4,090,987 | A | * | 5/1978 | Koerner et al. ........... 521/112 |
| 4,105,465 | A | * | 8/1978 | Berger ..................... 106/481 |
| 4,184,004 | A | * | 1/1980 | Pines et al. ............... 442/102 |
| 4,197,252 | A | * | 4/1980 | Joch et al. ................ 556/446 |
| 4,226,793 | A | | 10/1980 | Kotzsch et al. |
| 4,254,009 | A | * | 3/1981 | Dittrich et al. ........... 524/439 |
| 4,321,401 | A | * | 3/1982 | Nestler et al. ............ 556/457 |
| 4,399,247 | A | * | 8/1983 | Ona et al. ................ 524/204 |
| 4,504,410 | A | * | 3/1985 | Hempel et al. ........... 516/124 |
| 4,645,691 | A | * | 2/1987 | Ona et al. ................. 427/180 |
| 4,715,986 | A | * | 12/1987 | Gruning et al. .......... 516/100 |
| 4,891,154 | A | * | 1/1990 | Tesmann et al. ......... 516/124 |
| 5,004,559 | A | * | 4/1991 | Koerner et al. .......... 516/144 |
| 5,075,403 | A | | 12/1991 | Kirk |
| 5,306,856 | A | | 4/1994 | Streck et al. |
| 5,563,231 | A | * | 10/1996 | Barringer et al. ......... 528/26 |
| 5,591,818 | A | | 1/1997 | Standke et al. |
| 5,626,660 | A | * | 5/1997 | Lautenschlager et al. .............. 106/287.11 |
| 5,629,400 | A | | 5/1997 | Standke et al. |
| 5,679,147 | A | | 10/1997 | Standke et al. |
| 5,688,840 | A | * | 11/1997 | Ono ....................... 523/209 |
| 5,744,675 | A | | 4/1998 | Fiolitakis et al. |
| 5,808,125 | A | | 9/1998 | Standke et al. |
| 5,849,942 | A | | 12/1998 | Standke et al. |
| 5,863,509 | A | | 1/1999 | Standke et al. |
| 5,885,341 | A | | 3/1999 | Standke et al. |
| 5,932,757 | A | * | 8/1999 | Standke et al. .......... 556/457 |
| 6,018,011 | A | | 1/2000 | Scheim et al. |
| 6,020,448 | A | | 2/2000 | Jenkner et al. |
| 6,054,601 | A | | 4/2000 | Standke et al. |
| 6,118,015 | A | | 9/2000 | Haas et al. |
| 6,133,466 | A | | 10/2000 | Edelmann et al. |
| 6,139,622 | A | | 10/2000 | Gobel et al. |

(Continued)

FOREIGN PATENT DOCUMENTS
EP 0 692 567 1/1996

OTHER PUBLICATIONS

U.S. Appl. No. 11/995,215, filed Jan. 10, 2008, Jenkner, et al.
U.S. Appl. No. 11/995,751, filed Jan. 15, 2008, Edelmann, et al.
U.S. Appl. No. 11/995,550, filed Jan. 14, 2008, Edelmann, et al.
U.S. Appl. No. 11/572,555, filed Jan. 23, 2007, Just, et al.
U.S. Appl. No. 11/572,688, filed Jan. 25, 2007, Edelmann, et al.
U.S. Appl. No. 11/572,691, filed Jan. 25, 2007, Edelmann, et al.
U.S. Appl. No. 08/124,955, filed Sep. 21, 1993, Standke, et al.
U.S. Appl. No. 10/112,045, filed Apr. 1, 2002, Mehnert, et al.
U.S. Appl. No. 10/563,022, filed Dec. 30, 2005, Edelmann, et al.
U.S. Appl. No. 10/576,467, filed Apr. 20, 2006, Edelmann, et al.
U.S. Appl. No. 11/569,363, filed Nov. 20, 2006, Standke, et al.
U.S. Appl. No. 11/718,442, filed May 2, 2007, Standke.

(Continued)

Primary Examiner — Robert S Loewe
(74) Attorney, Agent, or Firm — Oblon, Spivak, McClelland, Maier & Neustadt, L.L.P.

(57) ABSTRACT

The present invention provides a linear, cyclic or branched polyether-functional siloxane or a mixture of polyether-functional siloxanes of the general formula (I) $R[—O_{(3-h)/2}Si(R^1)(OR)_h]_x[—O_{(3-i-j)/2}Si(R^2)(R^3)_i(OR)_j]_y$, (II) in which groups R are identical or different and R is essentially H, methyl, ethyl, n-propyl, isopropyl, n-butyl, isobutyl, t-butyl, 2-methoxyethyl or 2-hydroxyethyl or, in the case of cyclic siloxanes, may be a silyl radical of the silyl units of the formula (I), groups $R^1$ are identical or different and $R^1$ is a terminally blocked polyether group of the formula (II), $R_4—O[—R_5—O]_n[(—R^6)_m]—$ (II) and groups $R^2$ are identical or different and $R^2$ is a linear, branched or cyclic, optionally substituted alkyl group having 1 to 18 carbon atoms or a mercaptoalkyl group or an alkenyl group having 2 to 8 carbon atoms or an alkenyl group having 2 to 8 carbon atoms or an aryl group having 6 to 12 carbon atoms or an aminoalkyl group or the general formula (III) $H_2N(CH_2)_d[(NH)_e(CH_2)_f]_g—(CH_2)_3—$ (III) The present invention further provides aqueous and/or alcoholic compositions which comprise a polyether siloxane according to formula (I), to methods for the production of said systems, and to the use thereof.

13 Claims, No Drawings

U.S. PATENT DOCUMENTS

| | | | |
|---|---|---|---|
| 6,176,918 B1 | 1/2001 | Glausch et al. | |
| 6,177,582 B1 | 1/2001 | Jenkner et al. | |
| 6,211,284 B1 * | 4/2001 | Ishikawa et al. | 524/588 |
| 6,228,936 B1 | 5/2001 | Standke et al. | |
| 6,239,194 B1 * | 5/2001 | Standke et al. | 523/200 |
| 6,251,989 B1 | 6/2001 | Edelmann et al. | |
| 6,255,513 B1 * | 7/2001 | Standke et al. | 556/425 |
| 6,288,256 B1 | 9/2001 | Standke et al. | |
| 6,326,061 B1 * | 12/2001 | Lautenschlager et al. | 427/394 |
| 6,361,871 B1 | 3/2002 | Jenkner et al. | |
| 6,395,858 B1 | 5/2002 | Mack et al. | |
| 6,403,228 B1 | 6/2002 | Mack et al. | |
| 6,491,838 B1 | 12/2002 | Standke et al. | |
| 6,500,883 B1 * | 12/2002 | Mack et al. | 523/213 |
| 6,528,585 B1 | 3/2003 | Standke et al. | |
| 6,534,667 B1 | 3/2003 | Standke et al. | |
| 6,605,351 B1 * | 8/2003 | Rossmy et al. | 428/403 |
| 6,641,870 B2 | 11/2003 | Bartkowiak et al. | |
| 6,663,683 B2 | 12/2003 | Lortz et al. | |
| 6,676,719 B2 | 1/2004 | Lortz et al. | |
| 6,685,766 B2 | 2/2004 | Standke et al. | |
| 6,689,468 B2 | 2/2004 | Edelmann et al. | |
| 6,695,904 B2 | 2/2004 | Burger et al. | |
| 6,699,586 B2 | 3/2004 | Edelmann et al. | |
| 6,713,186 B1 | 3/2004 | Jenkner et al. | |
| 6,727,375 B2 | 4/2004 | Steding et al. | |
| 6,767,377 B2 | 7/2004 | Schumacher et al. | |
| 6,767,982 B2 * | 7/2004 | Standke et al. | 528/20 |
| 6,770,327 B2 | 8/2004 | Edelmann et al. | |
| 6,773,697 B2 | 8/2004 | Hemme et al. | |
| 6,773,814 B2 | 8/2004 | Schumacher et al. | |
| 6,808,769 B2 | 10/2004 | Batz-Sohn et al. | |
| 6,830,816 B2 | 12/2004 | Mehnert et al. | |
| 6,841,197 B2 | 1/2005 | Standke et al. | |
| 6,864,323 B2 | 3/2005 | Schlosser et al. | |
| 6,905,632 B2 | 6/2005 | Lortz et al. | |
| 6,946,537 B2 | 9/2005 | Krafczyk et al. | |
| 6,991,190 B2 | 1/2006 | Lortz et al. | |
| 7,015,270 B2 | 3/2006 | Scharfe et al. | |
| 7,026,398 B2 | 4/2006 | Monkiewicz et al. | |
| 7,083,769 B2 | 8/2006 | Moerters et al. | |
| 7,244,302 B2 | 7/2007 | Schumacher et al. | |
| 7,255,735 B2 | 8/2007 | Meyer et al. | |
| 7,374,787 B2 | 5/2008 | Lortz et al. | |
| 7,399,487 B2 | 7/2008 | Batz-Sohn et al. | |
| 7,423,165 B2 | 9/2008 | Korth et al. | |
| 7,427,442 B2 | 9/2008 | Albert et al. | |
| 7,470,423 B2 | 12/2008 | Lortz et al. | |
| 7,538,142 B2 | 5/2009 | Lortz et al. | |
| 7,572,854 B2 | 8/2009 | Schneider et al. | |
| 7,578,877 B2 | 8/2009 | Giessler et al. | |
| 7,611,753 B2 | 11/2009 | Bartkowiak et al. | |
| 7,615,577 B2 | 11/2009 | Lortz et al. | |
| 7,625,975 B2 | 12/2009 | Barfurth et al. | |
| 7,645,335 B2 | 1/2010 | Lortz et al. | |
| 7,749,322 B2 | 7/2010 | Schumacher et al. | |
| 7,780,777 B2 | 8/2010 | Perlet et al. | |
| 7,815,936 B2 | 10/2010 | Hasenzahl et al. | |
| 7,976,719 B2 | 7/2011 | Batz-Sohn et al. | |
| 8,012,367 B2 | 9/2011 | Hasenzahl et al. | |
| 2002/0098243 A1 | 7/2002 | Edelmann et al. | |
| 2002/0127415 A1 | 9/2002 | Standke et al. | |
| 2002/0197311 A1 | 12/2002 | Hasenzahl et al. | |
| 2003/0018155 A1 | 1/2003 | Krafczyk et al. | |
| 2003/0108580 A1 | 6/2003 | Hasenzahl et al. | |
| 2003/0134969 A1 | 7/2003 | Schlosser et al. | |
| 2003/0228271 A1 | 12/2003 | Batz-Sohn et al. | |
| 2004/0072704 A1 * | 4/2004 | Gerke et al. | 510/101 |
| 2004/0082736 A1 * | 4/2004 | Sakamoto et al. | 525/477 |
| 2004/0240062 A1 | 12/2004 | Lortz et al. | |
| 2005/0169861 A1 | 8/2005 | Lortz et al. | |
| 2005/0265934 A1 | 12/2005 | Schumacher et al. | |
| 2006/0063002 A1 | 3/2006 | Edelmann et al. | |
| 2006/0104881 A1 | 5/2006 | Lortz et al. | |
| 2006/0159635 A1 | 7/2006 | Meyer et al. | |
| 2006/0159636 A1 | 7/2006 | Meyer et al. | |
| 2006/0159637 A1 | 7/2006 | Meyer et al. | |
| 2006/0163533 A1 | 7/2006 | Batz-Sohn et al. | |
| 2006/0229210 A1 | 10/2006 | Neugebauer et al. | |
| 2006/0292192 A1 | 12/2006 | Hasenzahl et al. | |
| 2007/0054056 A1 | 3/2007 | Albert et al. | |
| 2007/0231280 A1 | 10/2007 | Schumacher et al. | |
| 2007/0297998 A1 | 12/2007 | Meyer et al. | |
| 2008/0027161 A1 | 1/2008 | Schlosser et al. | |
| 2008/0095724 A1 | 4/2008 | Hasenzahl et al. | |
| 2008/0188617 A1 * | 8/2008 | Standke et al. | 524/837 |
| 2008/0210130 A1 | 9/2008 | Giessler-Blank et al. | |
| 2008/0213325 A1 | 9/2008 | Schumacher et al. | |
| 2008/0249237 A1 | 10/2008 | Hager et al. | |
| 2008/0264299 A1 | 10/2008 | Lortz et al. | |
| 2009/0011246 A1 | 1/2009 | Giessler-Blank et al. | |
| 2009/0047225 A1 | 2/2009 | Hasenzahl et al. | |
| 2009/0131694 A1 | 5/2009 | Schumacher et al. | |
| 2009/0186053 A1 | 7/2009 | Meyer et al. | |
| 2009/0261309 A1 | 10/2009 | Lortz et al. | |
| 2010/0117021 A1 | 5/2010 | Batz-Sohn et al. | |
| 2010/0191001 A1 | 7/2010 | Wassmer et al. | |
| 2010/0209339 A1 | 8/2010 | Schumacher et al. | |
| 2010/0233392 A1 | 9/2010 | Batz-Sohn et al. | |
| 2010/0308287 A1 | 12/2010 | Lortz et al. | |
| 2011/0034584 A1 | 2/2011 | Albert et al. | |
| 2011/0045723 A1 | 2/2011 | Nowak et al. | |
| 2011/0071256 A1 | 3/2011 | Nowak et al. | |
| 2011/0259240 A1 | 10/2011 | Jenkner et al. | |

OTHER PUBLICATIONS

U.S. Appl. No. 11/815,391, filed Aug. 2, 2007, Standke, et al.
U.S. Appl. No. 11/814,127, filed Jul. 17, 2007, Standke, et al.
U.S. Appl. No. 12/159,785, filed Jul. 1, 2008, Standke, et al.
U.S. Appl. No. 12/281,629, filed Sep. 4, 2008, Militz, et al.
U.S. Appl. No. 12/673,390, filed Feb. 16, 2010, Wassmer, et al.
U.S. Appl. No. 12/674,271, filed Feb. 19, 2010, Albert, et al.
U.S. Appl. No. 12/673,777, filed Feb. 17, 2010, Kuehnle.
U.S. Appl. No. 12/678,299, filed Mar. 16, 2010, Borup, et al.
U.S. Appl. No. 12/161,112, filed Jul. 16, 2008, Standke, et al.
U.S. Appl. No. 12/596,725, filed Oct. 20, 2009, Giessler-Blank, et al.
U.S. Appl. No. 12/673,289, filed Feb. 12, 2010, Koschabek, et al.
U.S. Appl. No. 12/675,057, filed Feb. 24, 2010, Spyrou, et al.
U.S. Appl. No. 12/992,684, filed Mar. 4, 2011, Nowak, et al.
U.S. Appl. No. 13/058,290, filed Feb. 9, 2011, Weissenbach, et al.
U.S. Appl. No. 13/059,546, filed Feb. 17, 2011, Weissenbach, et al.
U.S. Appl. No. 13/062,225, filed Mar. 4, 2011, Weissenbach, et al.
U.S. Appl. No. 61/093,219, filed Aug. 29, 2008, Simoes.
U.S. Appl. No. 13/061,451, filed Feb. 28, 2011, Weissenbach, et al.
U.S. Appl. No. 13/011,115, filed Jan. 21, 2011, Ruf, et al.
U.S. Appl. No. 13/257,488, filed Oct. 21, 2011, Standke, et al.
U.S. Appl. No. 13/256,557, filed Sep. 14, 2011, Scharfe, et al.

* cited by examiner

POLYETHER-FUNCTIONAL SILOXANES, POLYETHER SILOXANE-CONTAINING COMPOSITIONS, METHODS FOR THE PRODUCTION THEREOF AND USE THEREOF

The present invention relates to novel polyether-functional siloxanes, to corresponding compositions, to the production thereof and to the use thereof.

Organosilanes and organofunctional siloxanes are nowadays important compounds for being able to change the properties of substrate surfaces.

Thus, for example, aminosilanes, such as DYNASYLAN® AMEO, or dilute solutions thereof in water are used for coating glass fibers in order to make them compatible and reactive toward organic resins.

In the context of more recent technologies, U.S. Pat. No. 6,716,771 discloses the hydrophilization of the surfaces of hydrophobic dielectrics by the CMP process using special aminofunctional silane systems.

In cases where alcohol must not be released during the application, as usually takes place during the hydrolysis and condensation of alkoxysilanes, it is also possible to use special water-based, essentially solvent-free alternatives, such as, for example, DYNASYLAN® 1151.

The production of aqueous organopolysilane-containing compositions is described, inter alia, in EP 1 031 593, EP 0 716 128, EP 0 716 127, EP 0 832 911 and EP 1 101 787. It is a common aspect of all of the disclosures that the solubility in water of such systems is brought about by the presence of aminofunctional groups in the organosiloxanes and/or the corresponding amino salts, such water-soluble siloxane systems being present in virtually completely hydrolyzed form in an aqueous preparation. Besides their chemical properties, such aqueous systems have the advantage of a comparatively low VOC content (VOC=volatile organic compound).

On the one hand, aminofunctional silanes and siloxanes can advantageously change the surface properties of substrates. However, the aminofunctionality can, on the other hand, due to its nucleophility and the reactivity associated therewith, also bring about undesired effects, e.g. bring about undesired resin curing. In addition, layers which contain compounds with aminogroups have a tendency to swell in a damp atmosphere.

Monomeric polyethersilanes are known per se (DE 26 32 719, EP 0 387 689). A distinction is made in principle between polyethersilanes with terminal hydroxy group and polyether silanes which are capped by an alkyl, aryl, alkenyl or alkynyl group. Polyether silanes with terminal hydroxy group or aqueous solutions thereof, as are described, for example, in U.S. Pat. No. 5,629,437, lead, due to strong polarity, in particular due to terminal hydroxy groups, to application problems which are comparable with those of aminosilanes.

The object of the invention was to provide a further way of enabling surface properties to be adjusted in a targeted manner. In particular, the aim was to improve the wettability of substrate surfaces.

The object set is achieved according to the invention in accordance with the features of the patent claims.

Surprisingly, novel polyether-functional organosiloxanes according to formula I below and/or corresponding organosiloxane mixtures (also called polyether siloxanes below) have been found which can be used advantageously as such, dissolved in water and/or alcohol, in a mixture with at least one monomeric organoalkoxysilane or corresponding preparation based thereon or the targeted treatment of substrate surfaces.

In particular, the hydrolysis alcohol can be removed from the system of aqueous solutions of present polyether siloxanes according to formula I, for example by distillation, advantageously giving a homogeneous, essentially solvent-free, i.e. low-VOC and environmentally friendly and user-friendly agent based on water for the targeted modification of substrate surfaces.

The present novel polyether siloxanes and compositions which comprise such polyether-functional siloxanes, moreover, bring about particularly good wettability of treated substrate surfaces.

The present invention thus provides a linear, cyclic or branched polyether-functional siloxane or a mixture of polyether-functional siloxanes of the general formula I

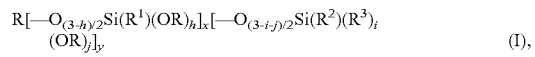

in which groups R are identical or different and R is essentially H, methyl, ethyl, n-propyl, isopropyl, n-butyl, isobutyl, t-butyl, 2-methoxyethyl or 2-hydroxyethyl or, in the case of cyclic siloxanes, may be a silyl radical of the silyl units of the formula I, groups $R^1$ are identical or different and $R^1$ is a terminally blocked polyether group of the formula II,

where $R^4$ is a linear, branched or cyclic alkyl group having 1 to 8 carbon atoms, preferably methyl, or an alkenyl group having 2 to 8 carbon atoms, preferably vinyl or alkyl, or an aryl group having 6 to 12 carbon atoms, preferably benzyl or phenyl or styryl, groups $R^5$ are identical or different and $R^5$ is a bivalent linear, branched or cyclic alkyl group having 1 to 8 carbon atoms, preferably methyl, ethyl, n-propyl, isopropyl, n-butyl or t-butyl, and $R^6$ is a bivalent linear, branched or cyclic alkyl group having 1 to 8 carbon atoms, preferably ethyl, n-propyl, isopropyl, n-butyl and isobutyl and n is 1 to 200, preferably 1 to 100, particularly preferably 2 to 40, in particular 3 to 30, and m is 0 or 1, groups $R^2$ are identical or different and $R^2$ is a linear, branched or cyclic, optionally substituted alkyl group having 1 to 18 carbon atoms, preferably methyl, ethyl, n-propyl, isopropyl, n-propyl, n-butyl, isobutyl, n-octyl, isooctyl, n-hexadecyl, n-octadecyl or fluoroalkyl, for example—but not exclusively—tridecafluoro-1,1,2,2-tetrahydrooctyl, or a mercaptoalkyl group, preferably 3-mercaptopropyl, or an alkenyl group having 2 to 8 carbon atoms, preferably vinyl, or an alkynyl group having 2 to 8 carbon atoms or an aryl group having 6 to 12 carbon atoms, preferably benzyl, phenyl or styryl, or an aminoalkyl group of the general formula III

where $0 \leq d \leq 6$, $0 \leq f \leq 6$, where e is 0, if d is 0, then g is 1, where e is 1, if d is >0, then g is 1 or 2, preferably 3-aminopropyl, N-(2-aminoethyl)-3-aminopropyl, 3-[2[(2-aminoethylamino)ethylamino]propyl, or an N-alkylaminoalkyl group, preferably N-(n-butyl)-3-aminopropyl, or an epoxyalkyl group, preferably 3-glycidyloxypropyl, or an acryloxyalkyl group, preferably 3-methacryloxypropyl, and $R^3$ is a linear, branched or cyclic alkyl group having 1 to 8 carbon atoms, preferably methyl, h, i and j, independently of one another, are the numbers 0 or 1, x is a number from 1 to 50, preferably 2 to 20, particularly preferably 3 to 10, and y is a number from 0 to 50, preferably 1 to 20, particularly preferably 3 to 10, where (x+y) is $\geq 2$ when y is >0 and (x+y) is >2 when y=0.

Polyether siloxanes and polyether siloxane mixtures according to the invention are generally clear to opaque, slightly to moderately viscous liquids.

In addition, polyethersiloxanes and polyethersiloxane mixtures according to the invention can advantageously be diluted, in particular—but not exclusively—with water and/or an alcohol. Further components can also be added to compositions obtained in this way. In addition, polyethersiloxanes according to the invention or their aqueous or alcohol-containing compositions can also be added to other surface-treatment compositions as further component.

The present invention therefore also provides a composition which comprises at least one alcohol, preferably methanol, ethanol and/or isopropanol, and a mixture of siloxanes according to the invention of the general formula I

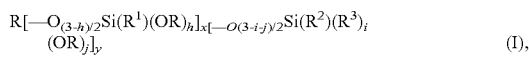

as already explained above in more detail.

Here, preference is given to alcoholic compositions which have an active ingredient content of siloxanes according to formula I of from 0.5 to 99.95% by weight, preferably 1 to 99.9% by weight, particularly preferably 5 to 99.5% by weight, in particular 10 to 98% by weight, based on the composition.

The present invention likewise provides a composition which comprises water and a mixture of siloxanes according to the invention of the general formula I

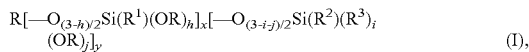

as has already been explained above in more detail.

Preferably, an aqueous composition according to the invention has an active ingredient content of siloxanes according to formula I of from 1 to 80% by weight, particularly preferably 5 to 70% by weight, in particular 20 to 60% by weight, based on the composition.

Such aqueous compositions can suitably be obtained as generally clear to opaque, readily mobile to moderately viscous liquids by mixing polyethersiloxanes of the invention according to formula I with water. In addition, hydrolysis alcohol produced during dilution can suitably be at least partly removed by distillation, where appropriate with fractionation and under reduced pressure. Such compositions according to the invention which are otherwise essentially free from organic solvents generally have an alcohol content of less than 5% by weight, preferably <2% by weight, particularly preferably $\leq 0.5\%$ by weight, in particular $\leq 0.1\%$ by weight, based on the composition. Here and below, the constituents of a composition in each case total 100% by weight.

The present invention further provides a composition which comprises a mixture of siloxanes according to the invention of the general formula I

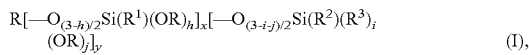

and at least one organoalkoxysilane from the series of alkylalkoxysilanes, preferably methyltrimethoxysilane, methyltriethoxysilane, n-propyltrimethoxysilane, n-propyltriethoxysilane, isobutyltrimethoxysilane and isobutyltriethoxysilane, arylalkoxy-silanes, preferably phenyltrimethoxysilane and phenyltriethoxysilane, silicic esters, preferably tetramethoxysilane, tetraethoxysilane and tetrapropyloxysilane, fluoro-alkylalkoxysilanes, preferably tridecafluoro-1,1,2,2-tetrahydrooctyltrimethoxysilane and tridecafluoro-1,1,2,2-tetrahydrooctyltriethoxysilane, aminoalkylalkoxysilanes, preferably 3-aminopropyltrimethoxysilane, 3-aminopropyltriethoxysilane, N-(2-aminoethyl)-3-aminopropyltrimethoxysilane, N,N-bis(2-aminoethyl)-3-aminopropyltrimethoxysilane, N—[N'-(2-aminoethyl)-2-aminoethyl]-3-aminopropyltrimethoxysilane, and N-(n-butyl)-3-aminopropyltrimethoxysilane, glycidyloxyalkylalkoxysilanes, preferably 3-glycidyloxypropyltrimethoxysilane and 3-glycidyloxypropyltriethoxysilane, methacryloxyalkylalkoxysilanes, preferably 3-methacryloxypropyltrimethoxysilane and 3-methacryloxyisobutyltrimethoxysilane, mercaptoalkylalkoxysilanes, preferably 3-mercaptotrimethoxysilane, or vinylalkoxysilanes, preferably vinyltrimethoxysilane, vinyltriethoxysilane and vinyltris(2-methoxyethoxy)silane, or a mixture of at least two of the abovementioned alkoxysilanes.

Besides polyether siloxanes according to the invention, compositions according to the invention can advantageously comprise at least one organoalkoxysilane or corresponding hydrolysates in an amount of from 0.1 to 99.9% by weight, preferably 99.8 to 90% by weight and 10 to 0.5% by weight, particularly preferably 99.5 to 95% by weight and 5 to 1% by weight, in particular 99.2 to 98% by weight and 4 to 2% by weight, based on the composition.

In addition, those compositions according to the invention which contain monomeric organosilane also suitably have a mixture of siloxanes according to formula I in an amount of from 0.1 to 99.9% by weight, based on the composition. In this connection, preference is given to contents of polyether siloxanes according to the invention of from 0.2 to 10% by weight and 90 to 99.5% by weight, particularly preferably 0.5 to 5% by weight and 95 to 99% by weight, in particular 0.8 to 2% by weight and 96 to 98% by weight, based on the composition.

The present invention further provides a method of producing polyether siloxanes according to the invention or a polyether siloxane-containing composition according to the invention by targeted hydrolysis, condensation or cocondensation of at least one monomeric hydrolyzable silane, where (i) at least one polyether alkoxysilane of the general formula IV

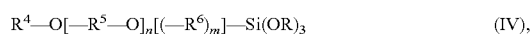

in which groups R are identical or different and R is methyl, ethyl, n-propyl, isopropyl, n-butyl, isobutyl, t-butyl, 2-methoxyethyl or 2-hydroxyethyl, $R^4$ is a linear, branched or cyclic alkyl group having 1 to 8 carbon atoms or an alkenyl group having 2 to 8 carbon atoms or an aryl group having 6 to 12 carbon atoms, groups $R^5$ are identical or different are $R^5$ is a bivalent linear, branched or cyclic alkyl group having 1 to 8 carbon atoms and $R^6$ is a bivalent linear, branched or cyclic alkyl group having 1 to 8 carbon atoms and n is 1 to 200, preferably 1 to 100, particularly preferably 2 to 40, in particular 3 to 30, and m is 0 or 1, or
(ii) at least one polyether alkoxysilane of the preceding formula IV and at least one organoalkoxysilane of the general formula V

$$R^2\text{—}Si(R^3)_i(OR)_{3-i} \qquad (V),$$

in which groups R are identical or different and R is methyl, ethyl, n-propyl, isopropyl, n-butyl, isobutyl, t-butyl, 2-methoxyethyl or 2-hydroxyethyl,
groups $R^2$ are identical or different and $R^2$ is a linear, branched or cyclic, optionally substituted alkyl group having 1 to 18 carbon atoms or
a mercaptoalkyl group or
an alkenyl group having 2 to 8 carbon atoms or
an alkinyl group having 2 to 8 carbon atoms or
an aryl group having 6 to 12 carbon atoms or
an aminoalkyl group of the general formula III

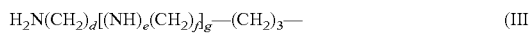

$$H_2N(CH_2)_d[(NH)_e(CH_2)_f]_g\text{—}(CH_2)_3\text{—} \qquad (III$$

where $0 \leq d \leq 6$, $0 \leq f \leq 6$, where e is 0, if d is 0, then g is 1, where e is 1, if d is >0, then g is 1 or 2, or
an N-alkylaminoalkyl group or
an epoxyalkyl group or
an acryloxyalkyl group and
$R^3$ is a linear, branched or cyclic alkyl group having 1 to 8 carbon atoms and
i is 0 or 1,
is reacted with 0.3 to 150 mol of water per mole of silane.

Preferably, the reaction according to the invention is carried out by adding from 0.5 to 100 mol, particularly preferably from 1 to 80 mol, very particularly preferably from 5 to 60 mol, in particular from 10 to 50 mol, of water.

This method generally gives a clear to opaque, slightly to moderately viscous liquid.

In addition, the reaction according to the invention can be carried out in the presence of a hydrolysis and/or condensation catalyst, for example in the presence of an organic or inorganic acid or a base. Preferably—but not exclusively—it is possible to use formic acid, acetic acid, hydrochloric acid, nitric acid, phosphoric acid or ammonia, alkali metal hydroxides, such as NaOH, KOH, LiOH, alkaline earth metal hydroxides, such as $Ca(OH)_2$, amines, such as triethylamine, alkoxides, such as $NaOCH_3$, $NaOC_2H_5$, $Mg(OCH_3)_2$, in particular corresponding aqueous acids or bases, and corresponding aqueous or alcoholic solutions.

In addition, an inert solvent, for example a corresponding alcohol with regard to the feed substances, preferably methanol, ethanol, n-propanol, isopropanol, 2-methylethanol or a mixture thereof, can be added to the reaction mixture of the reaction according to the invention.

In addition, in the method according to the invention, the reaction is carried out at a temperature in the range from 10 to 100° C., preferably at 30 to 90° C., in particular at 50 to 80° C.

Moreover, the reaction according to the invention is suitably carried out at a pH in the range from 1 to 12, preferably at 2 to 6 and 8 to 11, in particular at 3 to 5 and 9 to 10.5. For this, it is possible to use the methods known per se for determining the pH, for example pH paper, chemical methods with indicators or potentiometric methods, such as pH electrodes (cf. also R. Degner, S. Leibl, "pH messen. So wird's gemacht!", VCH, Weinheim, 1995).

In the method according to the invention, the silane of the general formula IV used is preferably at least one monomeric polyether silane from the series 3-[poly(ethylene glycol) monomethyl ether]propyltrialkoxysilane, 3-[poly(propylene glycol)mono-methylether]propyltrialkoxysilane, 3-[poly(ethylene glycol-co-propylene glycol) monomethyl ether]propyltrialkoxysilane or a mixture of at least two of the polyether alkoxysilanes, preference being given here to alkoxy groups from the series methoxy, ethoxy and propoxy.

In particular, preference is given here to polyether silanes according to formula IV, such as 3-[(polyethylene glycol) monomethyl ether]propyltriethoxysilane, 3-[(polyethylene glycol) monoethyl ether]propyltrimethoxysilane, 2-[(polyethylene glycol) monomethyl ether]ethyltrimethoxysilane, 3-[(polyethylene glycol) monobutyl ether]propyltrimethoxysilane and 5-[(polyethylene glycol) monomethyl ether]pentyltrimethoxysilane, as starting materials.

Such monomeric polyether silanes are generally a mixture, where the polyether groups with terminal blocking suitably have an average degree of polymerization of the repeat units of from 3 to 30, and where the bandwidth of the individual species, determined by analytically standard methods, for example by mass spectroscopy, ranges from preferably from 1 to 100, particularly preferably from 3 to 50, in particular from 4 to 40.

In addition, in the method according to the invention, the organoalkoxysilane of the general formula V used is preferably at least one silane from the series methyltrimethoxysilane, n-propyltrimethoxysilane, isobutyltrimethoxysilane, isobutyltriethoxysilane, octyltrimethoxysilane, hexadecyltrimethoxysilane, perfluoropropyltrimethoxysilane, tridecafluoro-1,1,2,2-tetrahydrooctyltrimethoxysilane, vinyltrimethoxysilane, vinylmethyldimethoxysilane, vinyltris(2-methoxyethoxy)silane, phenyltrimethoxysilane, 3-aminopropyltrimethoxysilane, 3-aminopropylmethyldimethoxysilane, N-(n-butyl)-3-amino propyltrimethoxysilane, N-(2-aminoethyl)-3-amino propyltrimethoxysilane, N-(2-aminoethyl)-3-aminopropylmethyldimethoxysilane, triaminoethylpropyltrimethoxysi lane, 3-mercaptopropyltrimethoxysilane, 3-glycidyloxypropyltrimethoxysilane, 3-methacryloxypropyltrimethoxysilane, 3-methacryloxy-2-methyl-propyltrimethoxysilane, methyltriethoxysilane, n-propyltriethoxysilane, octyltriethoxysilane, hexadecyltriethoxysilane, perfluoropropyltriethoxysilane, tridecafluoro-1,1,2,2-tetrahydrooctyltriethoxysilane, vinyltriethoxysilane, vinylmethyldiethoxysilane, phenyltriethoxysilane, 3-aminopropyltriethoxysilane, 3-aminopropylmethyldiethoxysilane, N-(n-butyl)-3-aminopropyltriethoxysilane, N-(2-aminoethyl)-3-aminopropyltriethoxysilane, N-(2-aminoethyl)-3-aminopropylmethyldiethoxysilane, triamino-ethylpropyltriethoxysilane, 3-mercaptopropyltriethoxysilane, 3-glycidyloxypropyltriethoxysilane, 3-methacryloxypropyltriethoxysilane, 3-methacryloxy-2-methylpropyltriethoxysilane or mixtures thereof.

In the method according to the invention, (a) the polyether silane according to formula IV and (b) the organoalkoxysilane according to formula V or a mixture of organoalkoxysilanes of the general formula V are advantageously used in a weight ratio (a) to (b) of from 0.5:100 to 100:0 preferably from 5:95 to 95:5, particularly preferably from 10:90 to 90:10, very particularly preferably from 25:75 to 75:25, in particular from 40:60 to 60:40, for example—but not exclusively—ratios of 98:2, 85:15, 80:20, 70:30, 50:50, but also 40:60 and 15:85, to name but a few.

In the present invention, particular preference is given to products, i.e. polyether siloxanes of the formula I according to the invention, which have the following combinations of functionalities:
3-[poly(ethylene glycol) monomethyl ether]propyl/hydroxy or methoxy, 3-[poly(ethylene glycol) monomethyl ether)propyl/hydroxy or ethoxy, 3-[poly(ethylene glycol) monomethyl ether]propyl/hydroxy or methoxy, ethoxy, 3-[poly(ethylene glycol) monomethyl ether]propyl/methoyl/ hydroxy or methoxy, 3-[poly(ethylene glycol) monomethyl ether]propyl/methyl/hydroxy or ethoxy, 3-[poly(ethylene glycol) monomethyl ether]propyl/vinyl/hydroxy or methoxy, 3-[poly(ethylene glycol) monomethyl ether]propyl/vinyl/hydroxy or ethoxy, 3-[poly(ethylene glycol) monomethyl ether] propyl/3-aminopropyl/hydroxy or methoxy, 3-[poly(ethylene glycol) monomethyl ether]propyl/3-aminopropyl/ hydroxy or ethoxy, 3-[poly(ethylene glycol) monomethyl ether]propyl/3-aminopropyl/hydroxy or methoxy, ethoxy, 3[poly(ethylene glycol) monomethyl ether]propyl/phenyl/ methoxy or hydroxy, 3-[poly(ethylene glycol) monomethyl ether)propyl/N-(2-aminoethyl)-3-aminopropyl/methoxy or hydroxy, 3-[poly(ethylene glycol) monomethyl ether]propyl/ N—(N'(2-aminoethyl)-2-aminoethyl]-3-aminopropyl/methoxy or hydroxy, 3-[poly(ethylene glycol) monomethyl ether] propyl/N-(n-butyl)-3-aminopropyl/methoxy or hydroxy, 3-[poly(ethylene glycol) monomethyl ether]propyl/3-methacryloxypropyl/methoxy or hydroxy, 3-[poly(ethylene glycol) monomethyl ether]propyl/3-glycidyloxypropyl/methoxy or hydroxy, 3-[poly(ethylene glycol) monomethyl ether]- propyl/tridecafluoro-1,1,2,2-tetrahydrooctyl/methoxy or hydroxy, 3-[poly(ethylene glycol) monomethyl ether]propyl/ octyl/tridecafluoro-1,1,2,2-tetrahydrooctyl/methoxy or hydroxy, 3-[poly(ethylene glycol) monomethyl ether]propyl/ propyl/tridecafluoro-1,1,2,2-tetrahydrooctyl/methoxy or hydroxy, 3-[poly(ethylene glycol) monomethyl ether]propyl/ methyl/tridecafluoro-1,1,2,2-tetrahydrooctyl/methoxy or hydroxy, 3-[poly(ethylene glycol) monomethyl ether]propyl/ vinyl/tridecafluoro-1,1,2,2-tetrahydrooctyl/methoxy or hydroxy, 3-[poly(ethylene glycol) monomethyl ether]propyl/ phenyl/tridecafluoro-1,1,2,2-tetrahydrooctyl/methoxy or hydroxy, 3-[poly(ethylene glycol) monomethyl ether]propyl/ 3-aminopropyl/tridecafluoro-1,1,2,2-tetrahydrooctyl/methoxy or hydroxy, 3-[poly(ethylene glycol)monomethyl ether] propyl/N-(n-butyl)-3-aminopropyl/tridecafluoro-1,1,2,2-tetrahydrooctyl/methoxy or hydroxy, 3-[poly(ethylene glycol) monomethyl ether]propyl/N-(2-aminoethyl)-3-aminopropyl/tridecafluoro-1,1,2,2-tetrahydrooctyl/methoxy or hydroxy, 3-[poly(ethylene glycol) monomethyl ether]propyl/ N,N-diaminoethyl-3-aminopropyl/tridecafluoro-1,1,2,2-tetrahydrooctyl/methoxy or hydroxy, 3-[poly(ethylene glycol) monomethyl ether]propyl/N,N'-diaminoethyl-3-aminopropyl/tridecafluoro-1,1,2,2-tetrahydrooctyl/methoxy or hydroxy, 3-[poly(ethylene glycol) monomethyl ether]-propyl/3-methacryloxypropyl/tridecafluoro-1,1,2,2-tetrahydrooctyl/methoxy or hydroxy, 3-[poly(ethylene glycol) monomethyl ether]propyl/3-glycidyloxypropyl/tridecafluoro-1,1,2,2-tetrahydrooctyl/methoxy or hydroxy, 3-[poly (ethylene glycol) monomethyl ether]propyl/phenyl/ethoxy or hydroxy, 3-[poly(ethylene glycol) monomethyl ether]propyl/ N-(2-aminoethyl)-3-aminopropyl/ethoxy or hydroxy, 3-[poly(ethylene glycol) monomethyl ether]propyl/N—[N'-(2-aminoethyl)-2-aminoethyl]-3-aminopropyl/ethoxy or hydroxy, 3-[poly(ethylene glycol) monomethyl ether]propyl/ N-(n-butyl)-3-aminopropyl/ethoxy or hydroxy, 3-[poly(ethylene glycol) monomethyl ether]propyl/3-methacryloxypropyl/ethoxy or hydroxy, 3-[poly(ethylene glycol) monomethyl ether]propyl/3-glycidyloxypropyl/ethoxy or hydroxy, 3-[poly(ethylene glycol) monomethyl ether]propyl/tridecafluoro-1,1,2,2-tetrahydrooctyl/ethoxy or hydroxy, 3-[poly (ethylene glycol) monomethyl ether]-propyl/octyl/tridecafluoro-1,1,2,2-tetrahydrooctyl/ethoxy or hydroxy, 3-[poly (ethylene glycol) monomethyl ether]propyl/propyl/ tridecafluoro-1,1,2,2-tetrahydrooctyl/ethoxy or hydroxy, 3-[poly(ethylene glycol) monomethyl ether]propyl/methyl/ tridecafluoro-1,1,2,2-tetrahydrooctyl/ethoxy or hydroxy, 3-[poly(ethylene glycol) monomethyl ether]propyl/vinyl/ tridecafluoro-1,1,2,2-tetrahydrooctyl/ethoxy or hydroxy, 3-[poly(ethylene glycol) monomethyl ether]propyl/phenyl/ tridecafluoro-1,1,2,2-tetrahydrooctyl/ethoxy or hydroxy, 3-[poly(ethylene glycol) monomethyl ether]propyl/3-aminopropyl/tridecafluoro-1,1,2,2-tetrahydrooctyl/ethoxy or hydroxy, 3-[poly(ethylene glycol) monomethyl ether]propyl/ N-(n-butyl)-3-aminopropyl/tridecafluoro-1,1,2,2-tetrahydrooctyl/ethoxy or hydroxy, 3-[poly(ethylene glycol) monomethyl ether]-propyl/N-(2-aminoethyl)-3-aminopropyl/tridecafluoro-1,1,2,2-tetrahydrooctyl/ethoxy or hydroxy, 3-[poly(ethylene glycol) monomethyl ether]propyl/N,N-diaminoethyl-3-aminopropyl/tridecafluoro-1,1,2,2-tetrahydrooctyl/ethoxy or hydroxy, 3-[poly(ethylene glycol) monomethyl ether]propyl/N,N'-diaminoethyl-3-aminopropyl/tridecafluoro-1,1,2,2-tetrahydrooctyl/ethoxy or hydroxy, 3-[poly(ethylene glycol) monomethyl ether]propyl/3-methacryloxypropyl/tridecafluoro-1,1,2,2-tetrahydrooctyl/ ethoxy or hydroxy, 3-[poly(ethylene glycol) monomethyl ether]propyl/3-glycidyloxypropyl/tridecafluoro-1,1,2,2-tetrahydrooctyl/ethoxy or hydroxy, 3-[poly(ethylene glycol) monomethyl ether]propyl/phenyl/methoxy, ethoxy or hydroxy, 3-[poly(ethylene glycol) monomethyl ether]propyl/ N-(2-aminoethyl)-3-aminopropyl/methoxy, ethoxy or hydroxy, 3-[poly(ethylene glycol) monomethyl ether]propyl/ N—[N'-(2-aminoethyl)-2-aminoethyl]-3-aminopropyl/ methoxy, ethoxy or hydroxy, 3-[poly(ethylene glycol) monomethyl ether]propyl/N-(n-butyl)-3-aminopropyl/methoxy, ethoxy or hydroxy, 3-[poly(ethylene glycol) monomethyl ether]propyl/3-methacryloxypropyl/methoxy, ethoxy or hydroxy, 3-[poly(ethylene glycol) monomethyl ether]propyl/3-glycidyloxypropyl/methoxy, ethoxy or hydroxy, 3-[poly(ethylene glycol) monomethyl ether]propyl/tridecafluoro-1,1,2,2-tetrahydrooctyl/methoxy, ethoxy or hydroxy, 3-[poly(ethylene glycol) monomethyl ether]propyl/octyl/ tridecafluoro-1,1,2,2-tetrahydrooctyl/methoxy, ethoxy or hydroxy, 3-[poly(ethylene glycol) monomethyl ether]propyl/ propyl/tridecafluoro-1,1,2,2-tetrahydrooctyl/methoxy, ethoxy or hydroxy, 3-[poly(ethylene glycol) monomethyl ether]propyl/methyl/tridecafluoro-1,1,2,2-tetrahydrooctyl/ methoxy, ethoxy or hydroxy, 3-[poly(ethylene glycol) monomethyl ether]propyl/vinyl/tridecafluoro-1,1,2,2-tetrahydrooctyl/methoxy, ethoxy or hydroxy, 3-[poly(ethylene glycol) monomethyl ether]propyl/phenyl/tridecafluoro-1,1, 2,2-tetrahydrooctyl/methoxy, ethoxy or hydroxy, 3-[poly (ethylene glycol) monomethyl ether]propyl/3-aminopropyl/ tridecafluoro-1,1,2,2-tetrahydrooctyl/methoxy, ethoxy or hydroxy, 3-[poly(ethylene glycol) monomethyl ether]propyl/ N-(n-butyl)-3-aminopropyl/tridecafluoro-1,1,2,2-tetrahydrooctyl/methoxy, ethoxy or hydroxy, 3-[poly(ethylene glycol) monomethyl ether]propyl/N-(2-aminoethyl)-3-amino propyl/tridecafluoro-1,1,2,2-tetrahydrooctyl/methoxy, ethoxy or hydroxy, 3-[poly(ethylene glycol) monomethyl ether]propyl/N,N-diaminoethyl-3-aminopropyl/tridecafluoro-1,1,2,2-tetrahydrooctyl/methoxy, ethoxy or hydroxy, 3-[poly(ethylene glycol) monomethyl ether]-propyl/N,N'-diaminoethyl-3-aminopropyl/tridecafluoro-1,1,2,2-tetrahydrooctyl/methoxy, ethoxy or hydroxy, 3-[poly(ethylene glycol) monomethyl ether]propyl/3-methacryloxypropyl/ tridecafluoro-1,1,2,2-tetrahydrooctyl/methoxy, ethoxy or hydroxy and 3-[poly(ethylene glycol) monomethyl ether] propyl/3-glycidyloxypropyl/tridecafluoro-1,1,2,2-tetrahydrooctyl/methoxy, ethoxy or hydroxy—to name but a few examples.

The method according to the invention is generally carried out by initially introducing the starting materials, i.e. the polyether silanes according to formula IV and the organoalkoxysilanes according to formula V and, with thorough mixing, adding water or a water/catalyst mixture in a targeted manner. It is also possible to dilute the starting material mixture used, for example by also adding a largely inert solvent, for example alcohol. However, it is also possible to initially introduce water or a water/alcohol mixture in which a catalyst is optionally present, and to meter in the starting silanes. In this connection, the pH of the reaction mixture should be in the range from 1 to 12. The reaction can generally be carried out at a temperature in the range from 10 to 100° C., it being possible, if necessary, to vary the pressure. In general, the reaction is carried out over a period from 5 minutes to 8 hours. The product mixture obtained in this way can then be left to after-react, if necessary at reflux with thorough mixing.

In addition, the alcohol added as diluent and also the alcohol produced by hydrolysis or condensation can essentially be at least partly removed from the product mixture by distillation. The distillation can be carried out with fractionation or, if necessary, under reduced pressure.

Moreover, the amount of alcohol which is removed from the system can at the same be replaced by a corresponding amount of water.

Polyether siloxane obtained in this way is generally a mixture of linear, cyclic and optionally branched siloxanes.

Polyether siloxane according to the invention or product mixture obtained according to the invention can then be diluted with water and/or alcohol in a targeted manner.

However, it is also possible to mix at least one specific organofunctional silane, preferably at least one organoalkoxysilane from the series of alkylalkoxysilanes, arylalkoxysilanes, silicic esters, fluoroalkylalkoxysilanes, aminoalkylalkoxysilanes, glycidyloxyalkylalkoxysilanes, methacryloxyalkylalkoxysilanes, mercaptoalkylalkoxysilanes or vinylalkoxysilanes with a polyether siloxane according to the invention, and to dilute this mixture as required if appropriate with water and/or alcohol.

However, it is also possible to additionally dilute the product mixture produced by the reaction carried out according to the invention with water and then—as already described above—to remove the alcohol from the aqueous system. In this way, it is possible to directly obtain a ready-to-use composition which contains water and polyether siloxane.

The present invention thus also provides polyether siloxanes according to the invention or corresponding siloxane mixtures or aqueous and/or alcoholic compositions according to the invention and compositions according to the invention which, besides polyether siloxanes, additionally comprise monomeric organosilanes which are obtainable by the present method.

Using products according to the invention, i.e. polyether siloxanes according to formula I and compositions according to the invention which comprise said polysiloxanes, it is possible, in a targeted and thus advantageous manner, to modify, and thus establish in a targeted manner, the surface properties of substrates from very hydrophobic to extremely hydrophilic. The wettability of the substrates to diverse liquid media can thus be controlled particularly advantageously.

Suitable substrates are, for example, but not exclusively, glass, quartz or silicon dioxide, ceramics, organically modified ceramics, speciality ceramics, such as SiC, SiOC, $Si_3N_4$, SiBN, SiBNC, BN, SiAlO, SiZrO, SiTiO, but also fillers and pigments, such as calcium sulfate, calcium carbonate, iron oxides, titanium oxides, aluminum oxides, silicon oxides, magnesium oxides, zirconium oxides, tin oxides, germanium oxides, zinc oxides, talc, kaolin, corundum, barite, wollastonite, indium-tin oxide, metals, such as iron, iron alloys, in particular steel, aluminum, aluminum alloys, titanium, titanium alloys, magnesium, magnesium alloys, copper, copper alloys, silver, silver alloys, gold, gold alloys, platinum, platinum alloys, polar plastics, such as, for example, polyesters or polyimide, polycarbonate, polyacrylates and polymethacrylates—to name but a few examples.

The preferably treated substrates also include layers produced by CVD and SPIN-on processes which, inter alia, can contain Si, O, C and N as such or in the form of corresponding compounds, in particular those layers which are used as dielectric in electronic components, i.e. on silicon surfaces, such as that of wafers. Thus, the treatment can here be carried out, for example, by the chemical-mechanical polishing of wafer surfaces during the manufacture of semiconductors.

Polyether siloxanes according to the invention or corresponding compositions according to the invention can be applied to a substrate surface for example—but not exclusively—by dipping, flow coating, sprinkling, spraying, centrifugation, polishing, doctoring, brushing, painting or collandering. Drying can then suitably take place at a temperature between 10 and 220° C., preferably between 20 and 150° C. This generally gives layers with a thickness of from 20 to 0.01 µm. The good wettability is usually evident as early as during application of the polyether-functional siloxanes according to the invention and of the compositions, as a result of which an extremely homogeneous layering can be achieved in a particularly advantageous manner. After drying the layer, the surface of the coated object or substrate can generally be coated very readily with polar to nonpolar media depending on how the composition of the condensates and/or cocondensates, i.e. the combination of the functionalities in the siloxanes, is chosen. Moreover, such layers are advantageously characterized by excellent adhesion promoting properties.

The present invention further provides the use of polyether siloxanes according to the invention and said compositions according to the invention for the treatment of substrate surfaces, i.e. in particular for a targeted modification of the properties of a surface, preferably of metals, such as silicon, aluminum, iron, titanium, magnesium, zinc, tin, copper, silver, gold, platinum, nickel, chromium, vanadium, tungsten, of alloys, such as iron alloys, steel, aluminum alloys, magnesium alloys, titanium alloys, copper alloys, silver alloys, gold alloys, platinum alloys, of conventional ceramics or speciality ceramics, such as SiC, SiOC, $Si_3N_4$, SiBN, SiBNC, BN, SiAlO, SiZrO, SiTiO, of artificial stone, of glass, of glass and mineral fibers, of construction materials, of building structures, as coating composition, as additive in coating compositions, as wetting agent for surfaces, as additive in wetting agents, as lubricant, as additive in lubricants, and in hydraulic fluids, as additive in drilling fluids, inter alia for borehole stabilization, as nonionic surfactant, e.g. in antifreezes and/or coolants, as impregnating agent, as additive in impregnating agents, as corrosion inhibitor, as additive in corrosion inhibitors, as antimisting agent, as additive in antimisting agents, as additive for paints and lacquers, as additive in cosmetic products, such as oil-in-water or water-in-oil emulsions, in the production of cosmetic products, in the production of compounds and composites, e.g. epoxy molding compounds, in the manufacture of wafers, semiconductors and chips, for the coating of optical lenses and of contact lenses, for the coating of electrolytic copper foils for printed circuit boards, for the silanization of fillers and pigments, such as calcium sulfate, calcium carbonate, iron oxides, titanium oxides, aluminum oxides, silicon oxides, magnesium oxides, zirconium oxides, tin oxides, germanium oxides, zinc oxides, talc, kaolin, corundum, barite, wollastonite, indium-tin oxide, and for the improvement of the rheological properties of dispersions.

The present invention thus also provides agents or articles based on the use according to the invention or use of a polyether siloxane according to the invention or a corresponding composition according to the invention.

The invention is illustrated in more detail by the examples below without limiting the subject-matter.

EXAMPLES

Reaction Apparatus for Carrying out the Examples 2 l stirred apparatus with reflux condenser, dropping funnel, mechanical stirrer and thermometer. For the distillation, the reflux condenser was exchanged for a distillation bridge with vacuum adapter. Turbidity which sometimes arose in the products following hydrolysis could be removed by filtration, for example via a pressure filter.

Silanes Used:
VPS 4140:

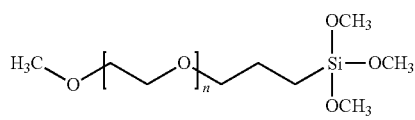

The polyether silane VPS 4140 has a molecular weight distribution. In the mass spectrum, species from n=6 to 30 are detected.

| DYNASYLAN ® F 8261: | tridecafluoro-1,1,2,2-tetrahydrooctyltriethoxysilane |
|---|---|
| DYNASYLAN ® AMEO: | 3-aminopropyltriethoxysilane |
| DYNASYLAN ® MTES: | methyltriethoxysilane |
| DYNASYLAN ® TRIAMO: | 3-[2-(2-aminoethylamino)-ethylamino]propyltrimetoxysilane |
| DYNASYLAN ® 1151: | aminofunctional siloxanes in water |
| DYNASYLAN ® HS 2775: | triaminofunctional siloxanes in water |

Example 1

Preparation of a Polyether Siloxane from Polyether Silane VPS 4140

800 g of demineralized water and 0.8 g of formic acid were initially introduced into the above-described apparatus, and 200 g of VPS 4140 were metered in over the course of 15 minutes. The mixture was then stirred for 1 hour at 70 to 75° C. At a bottom temperature of about 60° C., a methanol/water mixture was distilled off at a pressure of about 100 mbar until the top temperature was about 50° C. and the distillate only contained water. During the distillation, water was introduced in an amount corresponding to that of the product, as distillate was removed. When distillation was complete, the hydrolyzate remaining in the distillation flask was made up to 1000 g with demineralized water.

Example 2

Preparation of a Cocondensate of Polyether Silane VPS 4140 and DYNASYLAN® F 8261

114.6 g of DYNASYLAN® F 8261 and 285.4 g of VPS 4140 were initially introduced in 130 g of ethanol into the above-described apparatus and, at 50 to 75° C., demineralized water and 5.8 g of formic acid were metered in with vigorous stirring over the course of 7 hours. At a bottom temperature of about 45° C., a methanol/ethanol/water mixture was distilled off at a pressure of from 250 to 80 mbar until the top temperature was about 40° C. and the distillate only contained water. During the distillation, water was introduced in an amount corresponding to that of the product as distillate was removed. When the distillation was complete, the hydrolyzate remaining in the distillation flask was made up to 1000 g with demineralized water.

Example 3

Preparation of a Cocondensate of Polyether Silane VPS 4140 and DYNASYLAN® AMEO 600 g of demineralized water were initially introduced into the above-described apparatus, and a mixture of 296.6 g of VPS 4140 and 103.4 g of DYNASYLAN® AMEO was metered in over the course of 15 minutes. The mixture was then stirred for 2 hours at about 60° C. At a bottom temperature of about 60°, a methanol/ethanol/water mixture was distilled off at a pressure of from 150 to 100 mbar until the top temperature was about 50° C. and the distillate only contained water. During the distillation, water was introduced in an amount corresponding to that of the product as distillate was removed. When the distillation was complete, the hydrolyzate remaining in the distillation flask was made up to 1000 g with demineralized water.

Example 4

Preparation of a Cocondensate of Polyether Silane VPS 4140 and DYNASYLAN® MTES 600 g of demineralized water and 2.0 g of formic acid were initially introduced into the above-described apparatus, and a mixture of 312.4 g of VPS 4140 and 87.6 g of DYNASYLAN® MTES was metered in over the course of 15 minutes. The mixture was then stirred for 1.5 hours at 60 to 70° C. At a bottom temperature of about 60° C., a methanol/ethanol/water mixture was distilled off at a pressure of about 100 mbar until the top temperature was about 50° C. and the distillate contained only water. During the distillation, water was introduced in an amount corresponding to that of the product as distillate was removed. When the distillation was complete, the hydrolyzate remaining in the distillation flask was made up to 1000 g with demineralized water.

Example 5

Preparation of a Cocondensate of Polyether Silane VPS 4140 and DYNASYLAN® VTMO 600 g of demineralized water and 2.7 g of formic acid were initially introduced into the above-described apparatus, and a mixture of 324 g of VPS 4140 and 76 g of DYNASYLAN® VTMO was metered in over the course of 15 minutes. The mixture was then stirred for 2 hours at about 60° C. At a bottom temperature of about 55° C., a methanol/water mixture was distilled off at a pressure of from 140 to 90 mbar until the top temperature was about 50° C. and the distillate contained only water. During the distillation, water was introduced in an amount corresponding to that of the product as distillate was removed. When the distillation was complete, the hydrolyzate remaining in the distillation flask was made up to 1000 g with demineralized water.

Example 6

Preparation of a Cocondensate of Polyether Silane VPS 4140 and DYNASYLAN® TRIAMO 600 g of demineralized water were initially introduced into the above-described apparatus, and a mixture of 282 g of VPS 4140 and 118 g of DYNASYLAN® TRIAMO was metered in over the course of 15 minutes. The mixture was then stirred for 2 hours at about 60° C. At a bottom temperature of about 55° C., a methanol/water mixture was distilled off at a pressure of from 140 to 90 mbar until the top temperature was about 50° C. and the distillate contained only water. During the distillation, water was introduced in an amount corresponding to that of the product as distillate was removed. When the distillation was complete, the hydrolyzate remaining in the distillation flask was made up to 1000 g with demineralized water.

TABLE 1

Properties of the hydrolysis products prepared in examples 1 to 6:

| Hydrolysis product | Free methanol (% by wt.) | Free ethanol (% by wt.) | pH | Viscosity (20° C.) (mPa s)[1] | Color number (Gardner)[2] |
|---|---|---|---|---|---|
| Example 1 | <0.1 | — | 3.1 | 3.1 | 1 |
| Example 2 | <0.1 | <0.1 | 2.5 | 58.4 | 3 |
| Example 3 | <0.1 | <0.1 | 10.7 | 9.4 | 5 |
| Example 4 | <0.1 | <0.1 | 2.9 | 6.6 | 1 |
| Example 5 | <0.1 | — | 2.5 | 7.8 | 1 |
| Example 6 | <0.1 | — | 10.7 | 7.5 | 3 |

[1] DIN 53 015
[2] ISO 4630

Application and Comparison Examples 7 to 15

Glass wafers were degreased with acetone and polished with a cerium oxide slurry. The polyether siloxane-containing compositions prepared in examples 1 to 6 were polished onto the precleaned glass wafers. The wafers were then heat-treated at 150° C. for 60 minutes. The wettability and the surface energy of the modified wafer surfaces was quantified by means of contact angle measurements (static, $H_2O$) in accordance with DIN EN 828. The value given in table 2 in each case represented the average value of several measurements on a wafer.

As the examples according to table 2 reveal, using the optionally silane-modified polyether siloxane-containing compositions according to the invention it is possible to advantageously establish extremely variable surface properties, particularly in the area of low surface energy and very good wettability are new possibilities opened up.

TABLE 2

Results of application investigations on an untreated and surface-treated glass wafer.

| Example/comp. example | Treatment agent | Organofunctionalities of the siloxane and active ingredient | Contact angle θ [°] |
|---|---|---|---|
| 7 (blank value) | — | — | 33 ± 2° |
| 8 | from example 1 | polyether | 6 ± 1° |
| 9 | from example 3 | polyether/aminoalkyl | 20 ± 1° |
| 10 | from example 6 | polyether/triaminoalkyl | 25 ± 1° |
| 11 (comp. example) | DYNASYLAN® 1151 | aminoalkyl | 41 ± 4° |
| 12 | from example 5 | polyether/alkenyl | 44 ± 1° |
| 13 | from example 4 | polyether/alkyl | 61 ± 2° |
| 14 (comp. example) | DYNASYLAN® 2775 | triaminoalkyl | 62 ± 1° |
| 15 | from example 2 | polyether/fluoroalkyl | 91 ± 1° |

The invention claimed is:

1. A composition, comprising:
water; and
a mixture of siloxanes of formula I:

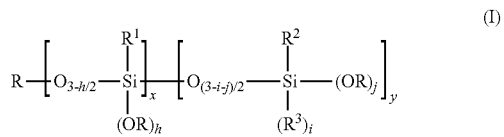

(I)

wherein
R is independently H, methyl, ethyl, n-propyl, isopropyl, n-butyl, isobutyl, t-butyl, 2-methoxyethyl or 2-hydroxyethyl; with the proviso that when a siloxane is cyclic R is optionally a silyl radical of formula:
$Si(R^1)(OR)_2$,
$R^1$ is independently a terminally blocked polyether group of the formula II,

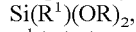

(II)

wherein
$R^4$ is a linear, branched or cyclic alkyl group having 1 to 8 carbon atoms or an alkenyl group having 2 to 8 carbon atoms or an aryl group having 6 to 12 carbon atoms,
$R^5$ is independently a bivalent linear, branched or cyclic alkyl group having 1 to 8 carbon atoms and
$R^6$ is a bivalent linear, branched or cyclic alkyl group having 1 to 8 carbon atoms and
n is 1 to 200 and
m is 1,
$R^2$ is independently a linear, branched or cyclic, optionally substituted alkyl group having 1 to 18 carbon atoms or
a mercaptoalkyl group or
an alkenyl group having 2 to 8 carbon atoms or
an alkynyl group having 2 to 8 carbon atoms or
an aryl group having 6 to 12 carbon atoms or
an aminoalkyl group of the general formula III

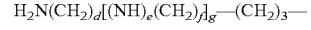

(III)

wherein $0 \leq d \leq 6$, $0 \leq f \leq 6$, where e is 0, if d is 0, then g is 1, where e is 1, if d is >0, then g is 1 or 2, or
an N-alkylaminoalkyl group or
an epoxyalkyl group or
an acryloxyalkyl group and
$R^3$ is a linear, branched or cyclic alkyl group having 1 to 8 carbon atoms and
h, i and j, independently of one another, are 0 or 1,
x is a number from 2 to 50 and y is a number from 1 to 50
wherein (x+y) is >2; and
wherein
a weight ratio of the repeating unit having the $R^1$ group to the repeating unit having the $R^2$ group in formula (I) is from 98/2 to 60/40,
the active ingredient content of siloxanes according to formula I is from 1 to 80% by weight, based on the weight of the composition; and
the content of alcohol is less than 5% by weight, based on the weight of the composition.

2. A composition, comprising:
a mixture of siloxanes of formula I:

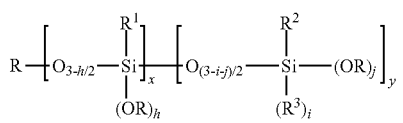

wherein
R is independently H, methyl, ethyl, n-propyl, isopropyl, n-butyl, isobutyl, t-butyl, 2-methoxyethyl or 2-hydroxyethyl; with the proviso that when a siloxane is cyclic R is optionally a silyl radical of formula:
$Si(R^1)(OR)_2$,
$R^1$ is independently a terminally blocked polyether group of the formula II,

wherein
$R^4$ is a linear, branched or cyclic alkyl group having 1 to 8 carbon atoms or an alkenyl group having 2 to 8 carbon atoms or an aryl group having 6 to 12 carbon atoms,
$R^5$ is independently a bivalent linear, branched or cyclic alkyl group having 1 to 8 carbon atoms and
$R^6$ is a bivalent linear, branched or cyclic alkyl group having 1 to 8 carbon atoms and
n is 1 to 200 and
m is 1,
$R^2$ is independently a linear, branched or cyclic, optionally substituted alkyl group having 1 to 18 carbon atoms or
a mercaptoalkyl group or
an alkenyl group having 2 to 8 carbon atoms or
an alkynyl group having 2 to 8 carbon atoms or
an aryl group having 6 to 12 carbon atoms or
an aminoalkyl group of the general formula III

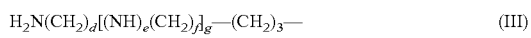

wherein $0 \leq d \leq 6$, $0 \leq f \leq 6$, where e is 0, if d is 0, then g is 1, where e is 1, if d is >0, then g is 1 or 2, or
an N-alkylaminoalkyl group or
an epoxyalkyl group or
an acryloxyalkyl group and
$R^3$ is a linear, branched or cyclic alkyl group having 1 to 8 carbon atoms and
h, i and j, independently of one another, are 0 or 1,
x is a number from 2 to 50 and
y is a number from 1 to 50
wherein (x+y) is >2;
and at least one organoalkoxysilane from the series of alkylalkoxysilanes, arylalkoxysilanes, silicic esters, fluoroalkoxysilanes, aminoalkylalkoxysilanes, glycidyl-oxyalkylalkoxysilanes, methacryloxyalkylalkoxysilanes, mercaptoalkylalkoxysilanes or vinylalkoxysilanes, wherein
a weight ratio of the repeating unit having the $R^1$ group to the repeating unit having the $R^2$ group in formula (I) is from 98/2 to 60/40,
said composition comprises at least one organoalkoxysilane in an amount of from 0.1 to 99.9% by weight, based on the weight of said composition; and
wherein said composition comprises a mixture of siloxanes according to formula I in an amount of from 0.1 to 99.9% by weight, based on the weight of said composition.

3. A method of producing siloxanes as claimed in claim 1 or 2 by targeted hydrolysis, condensation or cocondensation of at least one monomeric hydrolyzable organosilane, comprising:
(i) reacting at least one polyether alkoxysilane of formula IV and at least one organoalkoxy-silane of formula V with 0.3 to 150 mol of water per mole of silane:

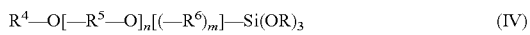

wherein R is independently methyl, ethyl, n-propyl, isopropyl, n-butyl, isobutyl, t-butyl, 2-methoxyethyl or 2-hydroxyethyl,
$R^4$ is a linear, branched or cyclic alkyl group having 1 to 8 carbon atoms or an alkenyl group having 2 to 8 carbon atoms or an aryl group having 6 to 12 carbon atoms,
$R^5$ is independently a bivalent linear, branched or cyclic alkyl group having 1 to 8 carbon atoms and
$R^6$ is a bivalent linear, branched or cyclic alkyl group having 1 to 8 carbon atoms and
n is 1 to 200 and
m is 1,

wherein
R is independently methyl, ethyl, n-propyl, isopropyl, n-butyl, isobutyl, t-butyl, 2-methoxyethyl or 2-hydroxyethyl,
$R^2$ is independently a linear, branched or cyclic, optionally substituted alkyl group having 1 to 18 carbon atoms or
a mercaptoalkyl group or
an alkenyl group having 2 to 8 carbon atoms or
an alkinyl group having 2 to 8 carbon atoms or
an aryl group having 6 to 12 carbon atoms or
an aminoalkyl group of formula III

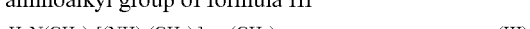

where $0 \leq d \leq 6$, $0 \leq f \leq 6$, where e is 0, if d is 0, then g is 1, where e is 1, if d is >0, then g is 1 or 2, or
an N-alkylaminoalkyl group or
an epoxyalkyl group or
an acryloxyalkyl group and
$R^3$ is a linear, branched or cyclic alkyl group having 1 to 8 carbon atoms and
i is 0 or 1,
wherein
a weight ratio of the at least one polyether alkoxysilane of formula IV to the at least one organoalkoxy-silane of formula V is from 98/2 to 60/40, and
a pH of reaction (i) or (ii) is from 1 to 12, and a hydrolysis and/or condensation catalyst is present.

4. The method as claimed in claim 3,
wherein
the reaction mixture comprises a solvent.

5. The method as claimed in claim 3,
wherein
0.5 to 100 mol of water are used per mole of at least one polyether alkoxysilane of formula IV and at least one organoalkoxy-silane of formula V.

6. The method as claimed in claim 3,
wherein
the reaction is carried out at a temperature in the range from 10 to 100° C.

7. The method as claimed in claim 3,
wherein
the silane of formula IV is at least one monomeric polyether silane selected from the group consisting of 3-[poly(ethylene glycol) monomethyl ether]propyltrialkoxysilane, 3-[poly(propylene glycol) monomethylether]propyltrialkoxysilane, 3-[poly(ethylene glycol-co-propylene glycol) monomethyl ether] propyltrialkoxysilane and a mixture threrof.

8. The method as claimed in claim 3,
wherein
the organoalkoxysilane of formula V is at least one silane selected from the group consisting of methyltrimethoxysilane, n-propyl trimethoxysilane, isobutyltrimethoxysilane, octyltrimethoxysilane, hexadecyltrimethoxysilane, perfluoropropyltrimethoxysilane, tridecafluoro-1,1,2,2-tetrahydrooctyltrimethoxysilane, vinyltrimethoxysilane, vinylmethyldimethoxysilane, vinyltris(2-methoxyethoxy)silane, phenyltrimethoxysilane, 3-mercaptopropyltrimethoxysilane, 3-gycidyloxypropyltrimethoxysilane, 3-methacryloxypropyltrimethoxysilane, 3-methacryloxy-2-methylpropyltrimethoxysilane, methyltriethoxysilane, n-propyltriethoxysilane, octyltriethoxysilane, hexadecyltriethoxysilane, perfluoropropyltriethoxysilane, tridecafluoro-1,1,2,2-tetrahydrooctyltriethoxysilane, vinyltriethoxysilane, vinylmethyldiethoxysilane, phenyltriethoxysilane, 3-mercaptopropyltriethoxysilane, 3-gycidyloxypropyltriethoxysilane, 3-methacryloxypropyltriethoxysilane, 3-methacryloxy-2-methylpropyltriethoxysilane and mixtures thereof.

9. The method as claimed in claim 3,
wherein
the weight ratio of the polyether silane according to formula IV to the organoalkoxysilane according to formula V or a mixture of organoalkoxysilanes of the general formula V is from 90/10 to 60/40.

10. The method as claimed in claim 3,
wherein
free alcohol and alcohol obtained from hydrolysis during the reaction are removed.

11. The method as claimed in claim 3,
further comprising at least one selected from the group consisting of:
(A) diluting the product mixture by a further addition of water, (B) diluting the product mixture by adding at least one alcohol and (C) adding at least one organoalkoxysilane selected from the group consisting of alkylalkoxysilanes, arylalkoxysilanes, silicic esters, fluoroalkylalkoxysilanes, aminoalkylalkoxysilanes, glycidyloxyalkylalkoxysilanes, methacryloxyalkylalkoxysilanes, mercaptoalkylalkoxysilanes and vinylalkoxysilanes to the product mixture.

12. The siloxanes as claimed in claim 1 or 2,
for the treatment of a surface,
as coating composition,
as additive in coating compositions,
as wetting agent for surfaces,
as additive in wetting agents,
as lubricant,
as additive in lubricants and in hydraulic fluids,
as nonionic surfactant,
as additive in drilling fluids,
as impregnating agent,
as additive in impregnating agents,
as corrosion inhibitor,
as additive in corrosion inhibitors,
as antimisting agent,
as additive in antimisting agents,
as additive for paints and lacquers,
as additive in cosmetic products,
in the production of cosmetic products,
in the production of composites,
in the production of compounds,
in the production of wafers, semiconductors and/or chips,
for the coating of optical lenses and of contact lenses,
for the coating of electrolytic copper foils for printed circuit boards,
for the silanization of fillers and pigments,
for the improvement of the rheological properties of dispersions.

13. An agent or article comprising the composition as claimed in claim 12.

* * * * *